US011723590B2

(12) United States Patent
Mountford (10) Patent No.: US 11,723,590 B2
(45) Date of Patent: Aug. 15, 2023

(54) METHOD AND SYSTEM FOR DETECTING AND IDENTIFYING ACUTE PAIN, ITS TRANSITION TO CHRONIC PAIN, AND MONITORING SUBSEQUENT THERAPY

(71) Applicant: Translational Research Institute Pty Ltd as trustee for Translational Research Institute Trust, Woolloongabba (AU)

(72) Inventor: Carolyn Mountford, Robina (AU)

(73) Assignee: DatChem, Brisbane (AU)

( * ) Notice: Subject to any disclaimer, the term of this patent is extended or adjusted under 35 U.S.C. 154(b) by 572 days.

(21) Appl. No.: 16/503,052

(22) Filed: Jul. 3, 2019

(65) Prior Publication Data
US 2020/0008741 A1   Jan. 9, 2020

Related U.S. Application Data

(60) Provisional application No. 62/694,258, filed on Jul. 5, 2018.

(51) Int. Cl.
| | |
|---|---|
| *A61B 5/00* | (2006.01) |
| *A61B 5/055* | (2006.01) |
| *G01R 33/48* | (2006.01) |
| *G01R 33/46* | (2006.01) |

(52) U.S. Cl.
CPC .......... *A61B 5/4824* (2013.01); *A61B 5/0042* (2013.01); *A61B 5/055* (2013.01); *G01R 33/4633* (2013.01); *G01R 33/4806* (2013.01); *A61B 5/4848* (2013.01)

(58) Field of Classification Search
CPC ..... A61B 5/4824; A61B 5/055; A61B 5/4848; G01R 33/20–64
See application file for complete search history.

(56) References Cited

U.S. PATENT DOCUMENTS

| | | | |
|---|---|---|---|
| 2012/0094318 A1* | 4/2012 | Orlando | C07K 14/705 435/7.1 |
| 2016/0089346 A1* | 3/2016 | Locke | A61B 5/1077 514/653 |

FOREIGN PATENT DOCUMENTS

| | | | | |
|---|---|---|---|---|
| WO | WO-2005036198 A1 * | 4/2005 | ........... | G01R 33/465 |
| WO | WO-2010073145 A1 * | 7/2010 | ......... | G01R 33/3614 |
| WO | WO-2013140106 A1 * | 9/2013 | ............ | A61B 5/377 |
| WO | 20015143070 A1 | 9/2015 | | |

OTHER PUBLICATIONS

Mountford, C. et al., "Six Fucose-α(1-2) Sugars and a-Fucose Assigned in Human Brain using In Vivo two-dimensional MRS", Dec. 22, 2014, NMR in Biomedicine, vol. 28.3, pp. 291-296 (Year: 2014).*

(Continued)

*Primary Examiner* — Yi-Shan Yang
*Assistant Examiner* — Tommy T Ly
(74) *Attorney, Agent, or Firm* — Lucas & Mercanti, LLP (57) ABSTRACT

The present invention relates to an MRS 1D or 2D method and system for obtaining spectral data of the brain of a subject and using neurochemical markers to enable whether a subject is experiencing acute pain, and providing the capacity to monitor response to therapy on an individual basis. The markers can be an increase of Fuc II, III, IV, VII and lactate.

20 Claims, 5 Drawing Sheets

(56) References Cited

OTHER PUBLICATIONS

A. P. Lin, S. Ramadan, P. Stanwell, T. Luu, J. Celestin, Z. Bajwa, and C. Mountford; "In vivo L-COSY MR Distinguishes Glutamate from Glutamine and Shows Neuropathic Pain to Cause a Buildup of Glutamine in the Brain", Proc. Intl. Soc. Mag. Reson. Med. 18 (2010), p. 381.

International Search Report dated Nov. 1, 2019 for PCT/IB2019/055769.

International Written Opinion dated Nov. 1, 2019 for PCT/IB2019/055769.

Siddall, P.J. et al., 'Magnetic Resonance Spectroscopy Detects Biochemical Changes in the Brain Associated with Chronic Low Back Pain: A Preliminary Report' Anesthesia and Analgesia, 2006, vol. 102, pp. 1164-1168.

Mountford, C. E., et al., MR spectroscopy in the breast clinic is improving. European Journal of Radiology, 2012. 81: p. S104-S106.

Lin A P, Ramadan S, Stern R A, Box H C, Nowinski C J, Ross B D, et al. Changes in the neurochemistry of athletes with repetitive brain trauma: preliminary results using localized correlated spectroscopy. Alzheimer's Research & Therapy. 2015; 7:13.

Borsook, D., et al., Neuroimaging revolutionizes therapeutic approaches to chronic pain. Mal Pain, 2007. 3: p. 25.

Ramadan S, et al., In Vivo Two Dimensional MR Spectroscopy Compares the Biochemistry of the Human Brain and Glioblastoma. Radiology, 2011. 259(2): p. 540-9.

Ross, J. M., et al., High brain lactate is a hallmark of aging and caused by a shift in the lactate dehydrogenase AIB ratio. Proceedings of the National Academy of Sciences, 2010.

Ramadan, S. and C. Mountford, Two Dimensional Magnetic Resonance Spectroscopy on Biopsy and In Vivo, in Annual Reviews in NMR, G Webb, Editor 2009, Academic Press.

Lean, C. L., et al., Cell-surface fucosylation and magnetic resonance spectroscopy characterization of human malignant colorectal cells. Biochemistry, 1992. 31(45): p. 11095-105.

* cited by examiner

METHOD AND SYSTEM FOR DETECTING AND IDENTIFYING ACUTE PAIN, ITS TRANSITION TO CHRONIC PAIN, AND MONITORING SUBSEQUENT THERAPY

CROSS-REFERENCE TO RELATED APPLICATIONS

This application claims priority to U.S. Provisional Application No. 62/694,258 filed Jul. 5, 2018, which is incorporated by reference herein.

TECHNICAL FIELD OF THE INVENTION

The present invention relates to a method and system for using neurochemical markers obtained by magnetic resonance spectroscopy (MRS) to identify acute pain, its transition to chronic pain, and providing the capacity to monitor response to therapy or treatment on an individual basis.

BACKGROUND OF THE INVENTION

This patent application cites various publications and other documents. These publications and documents are hereby incorporated by reference.

Evidence based medicine is currently used to manage acute pain i.e. each individual's clinical management is based on the outcomes from other people. The flaw in this approach is that risk of acute pain and response to treatment varies from person to person due to differences in genetic makeup, environmental exposure and insult to the body and type of pain. Personalized medicine is now being implemented from research outcomes where innovations are designed to customize care [1]. However its success is critically dependent on the reliability and increased precision for enabling diagnosis of acute pain, its transition to chronic pain, and monitoring therapy.

SUMMARY OF THE INVENTION

The present invention provides a system and method for using one-dimensional (1D) or two-dimensional (2D) MRS of the brain, and preferably 2D COrrelated SpectroscopY of the brain (2DCOSY), to detect acute pain and to predict and monitor its transition to chronic pain. The present invention is also directed to using 1D or 2D MRS, and preferably 2D MRS to detect neurochemical markers to identify acute pain, as distinguished from chronic pain. The method also provides a means to monitor the biochemical pathways as they either re-regulate or continue to de-regulate.

As used herein, the term "acute pain" means a type of pain that typically lasts less than 3 to 6 months or pain that is directly related to soft tissue damage such as lower back pain (LBP), a sprained ankle, paper cut, inflammation, a disease process or the result of surgery. Acute pain fades as whatever caused the pain is healed or resolved. Acute pain is distinguished from chronic pain and is relatively more sharp and severe. In contrast, the term "chronic pain" as used herein means pain that is usually ongoing and usually lasts more than 6 months, and is persistent.

MRS technology, in particular 2D MRS, allows definitive assignment of neurochemicals that alter with acute pain, its transition to chronic pain and response to therapy. The invention provides a system and method to apply MRS technologies to document the neurochemical effects of acute pain, and to monitor subsequent treatment therapy.

The MRS data can be analyzed by a modern informatics and now shown to be effective for a study on acute pain and its transitional changes. The outcome can yield informatics outcomes for automated specific molecular information on altered pathways for the development of improved, surgical or pharmacologic intervention; the capacity to monitor therapy; and tools for clinical assessment of recovery.

How acute pain alters brain chemistry can be monitored by neuromagnetic resonance spectroscopy (NMRS). In contrast to morphological magnetic resonance imaging (MRI), or functional MRI (fMRI) which characterizes temporal differences in brain activity in response to stimulation, NMRS monitors changes in the chemical activity in the brain. It is suggested [4] that NMRS identifies the earliest changes to the brain. NMRS can be correlated with modern techniques such as diffusion tensor imaging (DTI) and susceptibility weighted imaging (SWI).

In accordance with an embodiment of the present invention, acute pain of LBP was detected by obtaining MRS of the brain, by detecting the presence of an increase of fucosylated glycan Fuc II, III, IV and VII. Also, glutamatergic dysfunction is not observed in acute pain. The data can be evaluated either by conventional methods or by data mining creating a classifier.

After acute pain has been detected, and during and after one or more treatment periods, one can monitor the fucosylate glycans whose levels indicated acute pain, to see if those levels are returning to normal in response to treatment. The treatment can be the mere passage of time (also referred to as natural healing), and if the treatment is active, will involve positive treatment such as physiotherapy and/or medication for example.

The invention provides a method for enabling detection of whether a subject is experiencing acute pain, comprising: obtaining magnetic resonance spectra from a subject's brain tissue using a magnetic resonance spectroscopy device; and producing, from the magnetic resonance spectra obtained, spectral data which enables the detection of whether the subject is experiencing acute pain by detecting the presence of at least one neurochemical marker, by evaluating the data either by conventional methods or by data mining creating a classifier.

The invention provides a method for enabling detection of whether a subject is experiencing acute lower back pain, comprising: obtaining magnetic resonance spectra from a subject's brain tissue using a magnetic resonance spectroscopy device and either a 1D MRS or 2D COSY; and producing, from the magnetic resonance spectra obtained, spectral data which enables the detection of whether the subject is experiencing acute pain by detecting the presence of at least one neurochemical marker, the neurochemical marker being Fuc II, III, IV and Fuc VII and lactate, and wherein an increase of Fuc II, III, IV, VII and lactate, enables the detection of whether the subject is experiencing acute lower back pain, by evaluating the data either by conventional methods or by data mining creating a classifier.

The invention provides a system for using at least one neurochemical marker to enable detection of whether a subject is experiencing acute pain, comprising: a magnetic spectroscopy device for obtaining magnetic resonance spectra from a subject's brain tissue; and a processor for obtaining spectral data obtained from the magnetic resonance data, the spectral data having at least one neurochemical marker to enable a determination of whether the subject is experiencing acute pain, by evaluating the data either by conventional methods or by data mining creating a classifier.

The invention provides a computer readable storage medium for storing instructions that, when executed by a computer, produce, from magnetic resonance spectra obtained from a magnetic resonance spectroscopy of a subject's brain, spectral data which enables the detection of whether the subject is experiencing acute pain by detecting the presence of at least one neurochemical marker, by evaluating the data either by conventional methods or by data mining creating a classifier.

DESCRIPTION OF A PREFERRED EMBODIMENT

A description of a preferred embodiment of the invention will be described, but the invention will not be limited to this embodiment.

The invention provides a method for enabling detection of whether a subject is experiencing acute pain, comprising: obtaining magnetic resonance spectra from a subject's brain tissue using a magnetic resonance spectroscopy device; and producing, from the magnetic resonance spectra obtained, spectral data which enables the detection of whether the subject is experiencing acute pain by detecting the presence of at least one neurochemical marker, by evaluating the data either by conventional methods or by data mining creating a classifier.

The acute pain which can be detected may be lower back pain. The magnetic resonance spectra may be obtained using either a 1D MRS or 2D COSY. The neurochemical marker may be Fuc II, III, IV and Fuc VII and lactate, and wherein an increase of Fuc II, III, IV and Fuc VII and lactate in the spectral data enables the detection of whether the subject is experiencing acute pain. The neurochemical marker may be Fuc II, III, IV and Fuc VII and the spectral data enables the detection of whether the subject is experiencing acute pain. The neurochemical marker may be Fuc II, III, IV and Fuc VII, lactate, and wherein an increase of Fuc II, III, IV and Fuc VII and lactate in the spectral data, enables the detection of whether the subject is experiencing acute pain. The method may include the step of treating the patient with a treatment protocol to mitigate acute pain. The treatment protocol may include physiotherapy. The steps of obtaining and producing may be repeated after a time interval to monitor the progress of a treatment protocol. The time interval may be about 4 weeks. The steps of obtaining and producing may be repeated multiple times after time intervals, to monitor the progress of a treatment protocol. The step of producing may be performed in the cloud.

The invention provides a method for enabling detection of whether a subject is experiencing acute lower back pain, comprising: obtaining magnetic resonance spectra from a subject's brain tissue using a magnetic resonance spectroscopy device and either a 1D MRS or 2D COSY; and producing, from the magnetic resonance spectra obtained, spectral data which enables the detection of whether the subject is experiencing acute pain by detecting the presence of at least one neurochemical marker, the neurochemical marker being Fuc II, III, IV and Fuc VII and lactate, and wherein an increase of Fuc II, III, IV, VII and lactate, enables the detection of whether the subject is experiencing acute lower back pain, by evaluating the data either by conventional methods or by data mining creating a classifier.

The steps of obtaining and producing are repeated after a time interval to monitor the progress of a treatment protocol. The time interval may be about 4 weeks. The steps of obtaining and producing may be repeated multiple times after time intervals, to monitor the progress of a treatment protocol.

The invention provides a system for using at least one neurochemical marker to enable detection of whether a subject is experiencing acute pain, comprising: a magnetic spectroscopy device for obtaining magnetic resonance spectra from a subject's brain tissue; and a processor for obtaining spectral data obtained from the magnetic resonance data, the spectral data having at least one neurochemical marker to enable a determination of whether the subject is experiencing acute pain, by evaluating the data either by conventional methods or by data mining creating a classifier.

The acute pain which can be detected may be lower back pain. The magnetic resonance spectra may be obtained using either 1D MRS or 2D COSY. The neurochemical marker may be Fuc II, III, IV, VII and lactate, and wherein an increase of Fuc II, III, IV, VII and lactate, and enables the detection of whether the subject is experiencing acute pain. The neurochemical marker may be Fuc II, III, IV and Fuc V, and enables the detection of whether the subject is experiencing acute pain. The neurochemical marker may be Fuc II, III, IV, VII and lactate and wherein an increase of Fuc II, III, IV, VII and lactate enables the detection of whether the subject is experiencing acute pain. The system may include a memory for storing spectral data obtained during different time intervals to monitor the progress of a treatment protocol. The time interval may be about 4 weeks. The memory may store spectral data obtained multiple times after at least two time intervals, to monitor the progress of a treatment protocol.

The invention provides a computer readable storage medium for storing instructions that, when executed by a computer, produce, from magnetic resonance spectra obtained from a magnetic resonance spectroscopy of a subject's brain, spectral data which enables the detection of whether the subject is experiencing acute pain by detecting the presence of at least one neurochemical marker, by evaluating the data either by conventional methods or by data mining creating a classifier.

A 33-year-old woman with no history of low back pain (LBP) was recruited for this study. MRS of the brain was performed 30 hours after initial onset of pain and again during a treatment period 4 and 8 weeks later. Patient was receiving physiotherapy treatment during this treatment period. A 3T PRISMA scanner (Siemens Healthcare GmbH, Erlangen, Germany) equipped with a 64-channel head/neck coil was used to obtain the MRS data of the brain. It should be understood that scanners of other manufacturers could be used to obtain the data.

Figure 1:
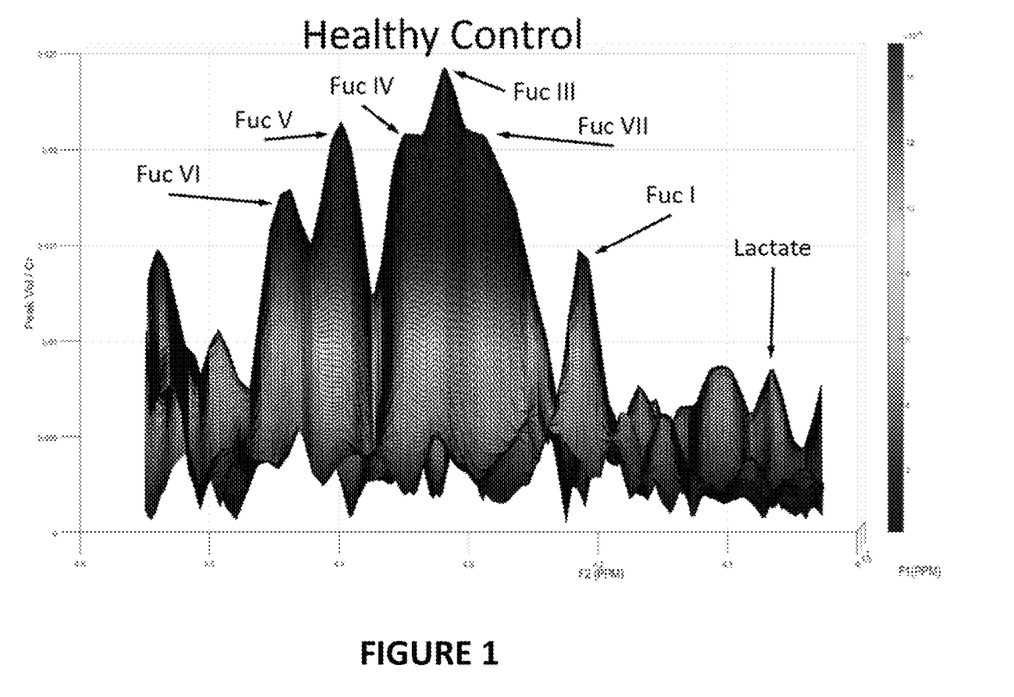
FIG. 1 is a 2D COSY of a brain spectrum of a normal healthy patient not experiencing acute pain.
Figure 2:
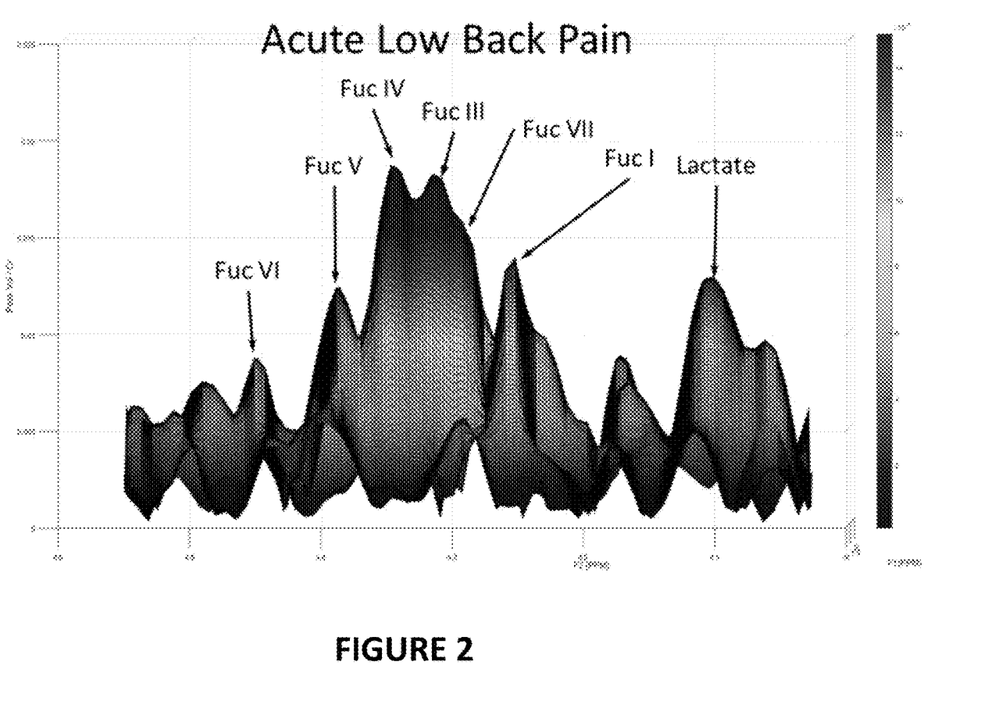
FIG. 2 is a 2D COSY of a brain spectrum of a patient with acute LBP.

FIG. 2 is a 2D COSY of a brain spectrum of a normal healthy patient not experiencing acute pain. FIG. 2 is a 2D COSY of a brain spectrum of a patient with acute LBP performed 30 hours after initial onset, and shows 3D Surface Plots from Spectral Region 4.0-4.6 & 0.9-1.6 ppm (referred to as the fucose region). Compared with a normal control (FIG. 1), in the acute phase, visual inspection of the 2D COSY spectrum demonstrates an increase in fucose species Fuc II, III, IV and VII and lactate, which indicates acute pain being experienced by the patient.

Figure 3:
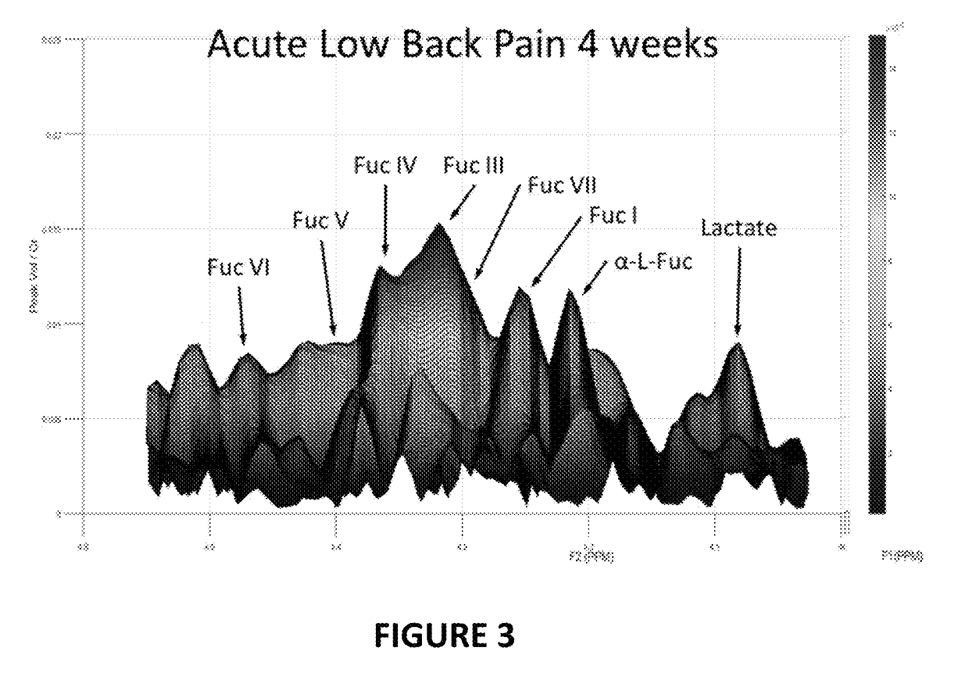
FIG. 3 is a 2D COSY of a brain spectrum of the patient of FIG. 2, but following diagnosis after 4 weeks of therapy.
Figure 4:
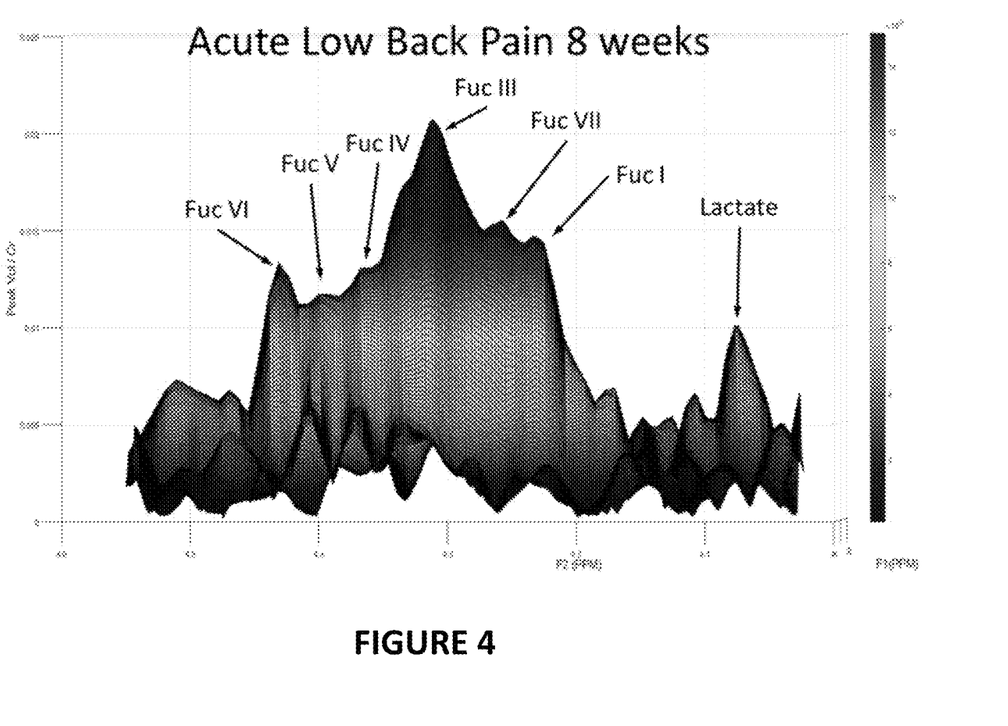
FIG. 4 is a 2D COSY of a brain spectrum of the same patient of FIGS. 1 & 2, but after 8 weeks of therapy.
Figure 5:
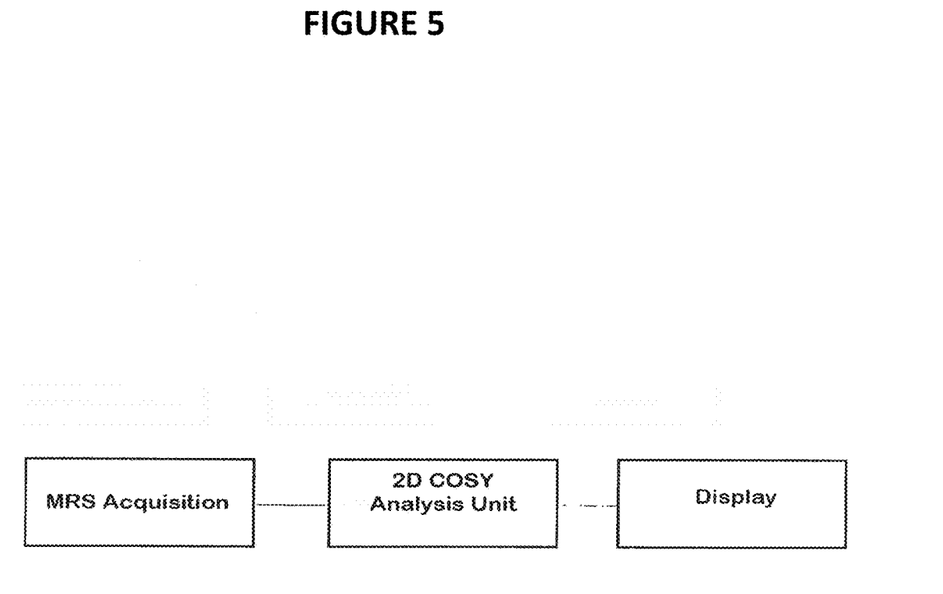
FIG. 5 is a block diagram of a system for enabling detection of acute pain using MRS.

As shown in FIG. 3, an overall decrease in the fucose region is seen 4 weeks after initial scan, after physiotherapy treatment. As shown in FIG. 4, at the 8 week scan after physiotherapy treatment, fucose species Fuc III, IV and Fuc VII levels appear within normal range.

Mountford et al have previously identified statistically significant differences in the fucosylated glycans in a number of disease cohorts including repetitive head trauma (2), PTSD and IBS (unpublished data). This case illustrates the potential for 2D COSY to determine acute LBP in association with neurochemical deregulation, by detecting Fuc II, III, IV, VII and lactate. In the case of response to therapy the repopulation of the fucosylated glycans can be recorded.

In this particular study, fucose molecules changed and were a marker for acute pain. However, the marker molecules may differ according to whether the pain to be detected is of inflammatory, nociceptive or neuropathic origin.

The method and system of the analysis of the data obtained by MRS may be performed locally at the location of the MRS device, or the data may be communicated to a different location for analysis, such as in the cloud of a computing system. The data can also be obtained using 1D spectroscopy. The steps performed may be implemented in a system using a memory device which stores program steps for executing the method in a non-volatile memory, such as a CD, thumb drive or other storage device.

Although one embodiment has been disclosed, the invention is not limited to this embodiment, and the scope of the invention is defined by way of the appended claims.

REFERENCES INCORPORATED BY REFERENCE, AND IN SOME CASES CITED

1. Siddall P J, Stanwell P, Woodhouse A, Somorjai R L, Dolenko B, Nikulin A, et al. Magnetic resonance spectroscopy detects biochemical changes in the brain associated with chronic low back pain: a preliminary report. Anesthesia and analgesia. 2006; 102(4):1164-8.
2. Lin A P, Ramadan S, Stern R A, Box H C, Nowinski C J, Ross B D, et al. Changes in the neurochemistry of athletes with repetitive brain trauma: preliminary results using localized correlated spectroscopy. Alzheimer's Research & Therapy. 2015; 7:13.
3. Weston A D and Hood L, *Systems Biology, Proteomics, and the Future of Health Care: Toward Predictive, Preventative, and Personalized Medicine*. J Proteome Res, 2004. 3(2): p. 179-196.
4. Cousins, M. (2012) http://www.painaustralia.org.au/about-us/who-we-are.html. Pain Australia.
5. *The high price of pain: the economic impact of persistent pain in Australia November* 2007 2007, MBF Foundation in collaboration with University of Sydney Pain Management Research Institute.
6. Borsook, D., et al., *Neuroimaging revolutionizes therapeutic approaches to chronic pain*. Mol Pain, 2007. 3: p. 25.
7. Rodriguez, M. A., N. Afari, and D. S. Buchwald, *Evidence for overlap between urological and nonurological unexplained clinical conditions*. J Urol, 2009. 182(5): p. 2123-31.
8. Prescot A, et al., *Excitatory neurotransmitters in brain regions in interictal migraine patients*. Molecular Pain, 2009. 5(34).
9. Siddall, P. J., et al., *Magnetic resonance spectroscopy detects biochemical changes in the brain associated with chronic low back pain: A preliminary report*. Anesthesia and Analgesia, 2006. 102(4): p. 1164-1168.
10. Stanwell P, et al., *Neuro magnetic resonance spectroscopy using wavelet decomposition and statistical testing identifies biochemical changes in people with spinal cord injury and pain*. NeuroImage, 2010. 53.(2): p. 544-52.
11. Ramadan S, et al., *In Vivo Two Dimensional MR Spectroscopy Compares the Biochemistry of the Human Brain and Glioblastoma*. Radiology, 2011. 259(2): p. 540-9.
12. Wolf C J, *Pain: Moving from Symptom Control toward Mechanism-Specific Pharmacologic Management*. Annals of Internal Medicine PHYSIOLOGY IN MEDICINE: A SERIES OF ARTICLES LINKING MEDICINE WITH SCIENCE Physiology in Medicine, 2004. 140: p. 441-451.
13. Labus J S, et al., *Acute tryptophan depletion alters the effective connectivity of emotional arousal circuitry during visceral stimuli in healthy women*. Gut, 2011. 60(9): p. 1196-203.
14. Wolf C J, *Central sensitization: implications for the diagnosis and treatment of pain*. Pain, 2011. 152(S2-15).
15. Grachev, I. D., B. E. Fredrickson, and A. V. Apkarian, *Abnormal brain chemistry in chronic back pain: an in vivo proton magnetic resonance spectroscopy study*. Pain, 2000. 89(1): p. 7-18.
16. Fukui, S., Matsuno, M., Inubushi, T., Nosaka, S., *N-Acetylaspartate concentrations in the thalami of neuropathic pain patients and healthy comparison subjects measured with 1H-MRS*. Magn. Reson. Imaging, 2006. 24: p. 75-79.
17. Carder, R. K. and S. H. Hendry, *Neuronal characterization, compartmental distribution, and activity-dependent regulation of glutamate immunoreactivity in adult monkey striate cortex*. J. Neurosci, 1994. 14: p. 242-262.
18. Ross, J. M., et al., *High brain lactate is a hallmark of aging and caused by a shift in the lactate dehydrogenase A/B ratio*. Proceedings of the National Academy of Sciences, 2010.
19. Murrey H E, et al., *Identification of the Plasticity-Relevant Fucose-α(1-2)Galactose Proteome from the Mouse Olfactory Bulb*. Biochemistry, 2009. 48(30): p. 7261-7270.
20. De Graaf T W, et al., *Inflammation-induced expression of sialyl Lewis X-containing glycan structures on alpha 1-acid glycoprotein (orosomucoid) in human sera*. J Experimental Med, 1993. 177(3): p. 657-666.
21. Smalla, K. H., et al., *Identification of fucose-alpha[1-2]-galactose epitope containing glycoproteins from rat hippocampus*. Neuroreport, 1998. 9: p. 813-817.
22. Hoeche N, et al. *Mapping fucosylated synaptic proteins*. in *FENS Forum* 2010. Amsterdam.
23. Lowe J B, *Glycan-dependent leukocyte adhesion and recruitment in inflammation*. Curr Opin Cell Biol, 2003. 15: p. 531-538.
24. Ramadan, S. and C. Mountford, *Two Dimensional Magnetic Resonance Spectroscopy on Biopsy and In Vivo*, in *Annual Reviews in NMR*, G. Webb, Editor. 2009, Academic Press.
25. Chamoun, R., et al., *Role of extracellular glutamate measured by cerebral microdialysis in severe traumatic brain injury*. J Neurosurg, 2010.

26. Lipton S A and Rosenberg P A, *Excitatory Amino Acids as a Final Common Pathway for Neurologic Disorders*. N Engl J Med, 1994. 330: p. 613-622.
27. Lean, C. L., et al., *Cell-surface fucosylation and magnetic resonance spectroscopy characterization of human malignant colorectal cells*. Biochemistry, 1992. 31(45): p. 11095-105.
28. Mountford, C. E., et al., *MR spectroscopy in the breast clinic is improving*. European Journal of Radiology, 2012. 81: p. S104-S106.

I claim:

1. A method for enabling detection of whether a subject is experiencing acute pain, comprising:
    obtaining magnetic resonance spectra from the subject's brain tissue using a magnetic resonance spectroscopy (MRS) device; and
    producing, from the magnetic resonance spectra obtained, spectral data;
    detecting, from the spectral data, presence of neurochemical markers, wherein the neurochemical markers are Fuc II, Fuc III, Fuc IV, Fuc VII and lactate;
    detecting whether there is an increase for each of the neurochemical markers by comparing the spectral data of the subject to spectral data of a normal control; and
    determining that the subject is experiencing the acute pain when the increase of Fuc II, Fuc III, Fuc IV, Fuc VII and lactate is detected in the spectral data.

2. The method of claim 1, wherein the magnetic resonance spectra is obtained using either a one-dimensional (1D) MRS or two-dimensional correlated spectroscopy 2D COSY).

3. The method of claim 1, further comprising treating the subject with a treatment protocol to mitigate the acute pain.

4. The method of claim 3, wherein the treatment protocol includes physiotherapy.

5. The method of claim 1, wherein the steps of obtaining, producing, detecting, and determining are repeated after a time interval to monitor progress of a treatment protocol.

6. The method of claim 5, wherein the time interval is 4 weeks.

7. The method of claim 1, wherein the steps of obtaining, producing, detecting, and determining are repeated multiple times after time intervals, to monitor the progress of a treatment protocol.

8. The method of claim 1, wherein the step of producing is performed in a cloud of a computing system.

9. A method for enabling detection of whether a subject is experiencing acute lower back pain, comprising:
    obtaining magnetic resonance spectra from the subject's brain tissue using a magnetic resonance spectroscopy (MRS) device and either a one-dimensional (1D) MRS or two-dimensional correlated spectroscopy (2D COSY);
    producing, from the magnetic resonance spectra obtained, spectral data;
    detecting, from the spectral data, presence of neurochemical markers, wherein the neurochemical markers are Fuc II, Fuc III, Fuc IV, Fuc VII and lactate;
    detecting whether there is an increase for each of the neurochemical markers by comparing the spectral data of the subject to spectral data of a normal control; and
    determining that the subject is experiencing the acute lower back pain when the increase of Fuc II, Fuc III, Fuc IV, Fuc VII and lactate is detected in the spectral data.

10. The method of claim 9, wherein the steps of obtaining, producing, detecting, and determining are repeated after a time interval to monitor progress of a treatment protocol.

11. The method of claim 10, wherein the time interval is 4 weeks.

12. The method of claim 9, wherein the steps of obtaining, producing, detecting, and determining are repeated multiple times after time intervals, to monitor progress of a treatment protocol.

13. A system for using a plurality of neurochemical markers to enable detection of whether a subject is experiencing acute pain, comprising:
    a magnetic resonance spectroscopy (MRS) device for obtaining magnetic resonance spectra from the subject's brain tissue; and
    a processor configured to
    produce, from the magnetic resonance spectra obtained, spectral data;
    detect, from the spectral data, presence of neurochemical markers, wherein the neurochemical markers are Fuc II, Fuc III, Fuc IV, Fuc VII and lactate;
    detect whether there is an increase for each of the neurochemical markers by comparing the spectral data of the subject to spectral data of a normal control; and
    determine that the subject is experiencing the acute pain when the increase of Fuc II, Fuc III, Fuc IV, Fuc VII and lactate is detected in the spectral data.

14. The system of claim 13, wherein the magnetic resonance spectra is obtained using either one-dimensional (1D) MRS or two-dimensional correlated spectroscopy 2D COSY).

15. The system of claim 13, including a memory for storing spectral data obtained during different time intervals to monitor progress of a treatment protocol.

16. The system of claim 15, wherein the time interval is 4 weeks.

17. The system of claim 15, wherein the memory stores spectral data obtained multiple times after at least two time intervals, to monitor the progress of the treatment protocol.

18. A computer readable non-transitory storage medium for storing instructions that, when executed by a computer, performs a method for enabling detection of whether a subject is experiencing acute pain, the method comprising steps of
    producing spectral data from magnetic resonance spectra obtained from using a magnetic resonance spectroscopy (MRS) device;
    detecting, from the spectral data, presence of neurochemical markers, wherein the neurochemical markers are Fuc II, Fuc III, Fuc IV, Fuc VII and lactate;
    detecting whether there is an increase for each of the neurochemical markers by comparing the spectral data of the subject to spectral data of a normal control; and
    determining that the subject is experiencing the acute pain when the increase of Fuc II, Fuc III, Fuc IV, Fuc VII and lactate is detected in the spectral data.

19. A method for enabling detection of whether a subject is experiencing acute pain, comprising:
    obtaining magnetic resonance spectra from the subject's brain tissue using a magnetic resonance spectroscopy (MRS) device; and
    producing, from the magnetic resonance spectra obtained, spectral data;
    detecting, from the spectral data, the presence of a neurochemical marker, wherein the neurochemical marker is Fuc VII; and detecting whether there is an increase for the neurochemical marker by comparing the spectral data of the subject to spectral data of a normal control; and determining that the subject is experiencing the acute pain when the increase of Fuc VII is detected in the spectral data.

20. A system for using a neurochemical marker to enable detection of whether a subject is experiencing acute pain, comprising:

a magnetic resonance spectroscopy (MRS) device for obtaining magnetic resonance spectra from the subject's brain tissue; and a processor configured to produce, from the magnetic resonance spectra obtained, spectral data;

detect, from the spectral data, presence of a neurochemical marker, wherein the neurochemical marker is Fuc VII;

detect whether there is an increase for each of the neurochemical markers by comparing the spectral data of the subject to spectral data of a normal control; and determine that the subject is experiencing the acute pain when the increase of Fuc VII is detected in the spectral data.

* * * * *